United States Patent [19]

Mitchell

[11] Patent Number: 4,704,117
[45] Date of Patent: * Nov. 3, 1987

[54] FORMED AND WASHABLE DIAPER

[75] Inventor: Debra J. Mitchell, Piedmont, Calif.

[73] Assignee: Ernest H. McCoy, Albany, Calif.

[*] Notice: The portion of the term of this patent subsequent to May 14, 2002 has been disclaimed.

[21] Appl. No.: 821,876

[22] Filed: Jan. 27, 1986

Related U.S. Application Data

[63] Continuation-in-part of Ser. No. 588,349, Mar. 12, 1984, Pat. No. 4,516,975 and a continuation-in-part of Ser. No. 660,062, Nov. 12, 1984, abandoned.

[51] Int. Cl.$^4$ ............................................. A61F 13/16
[52] U.S. Cl. .................................................... 604/391
[58] Field of Search ............... 604/383, 379, 378, 372, 604/390, 391, 385.1, 385.2

[56] References Cited

U.S. PATENT DOCUMENTS

| | | |
|---|---|---|
| Re. 30,972 | 6/1982 | Kyle et al. ........................... 604/383 |
| 3,141,461 | 7/1964 | Farris .................................. 604/391 |
| 3,481,337 | 12/1969 | Ruffo ................................ 604/385 R |
| 4,338,938 | 7/1982 | Seavitt ............................... 604/385 A |
| 4,397,646 | 8/1983 | Daniels et al. ....................... 604/386 |
| 4,402,690 | 9/1983 | Redfein ............................. 604/385.2 |
| 4,410,327 | 10/1983 | Baggaley ............................. 604/391 |
| 4,516,975 | 5/1985 | Mitchell ........................... 604/385 A |

Primary Examiner—John D. Yasko
Attorney, Agent, or Firm—Bruce & McCoy

[57] ABSTRACT

A formed and washable diaper comprised of multiple layers of material including an inner layer of soft non-irritating absorbent washable fabric, an absorbent and moisture retentative mildew-resistant washable felt layer, and an outer moisture barrier layer of fabric, said diaper being formed with a configuration which is body-fitting and includes extra absorbency material disposed from front to rear of the wearer's body in the crotch area and which conforms thereto due to the unique method of construction of the diaper.

7 Claims, 7 Drawing Figures

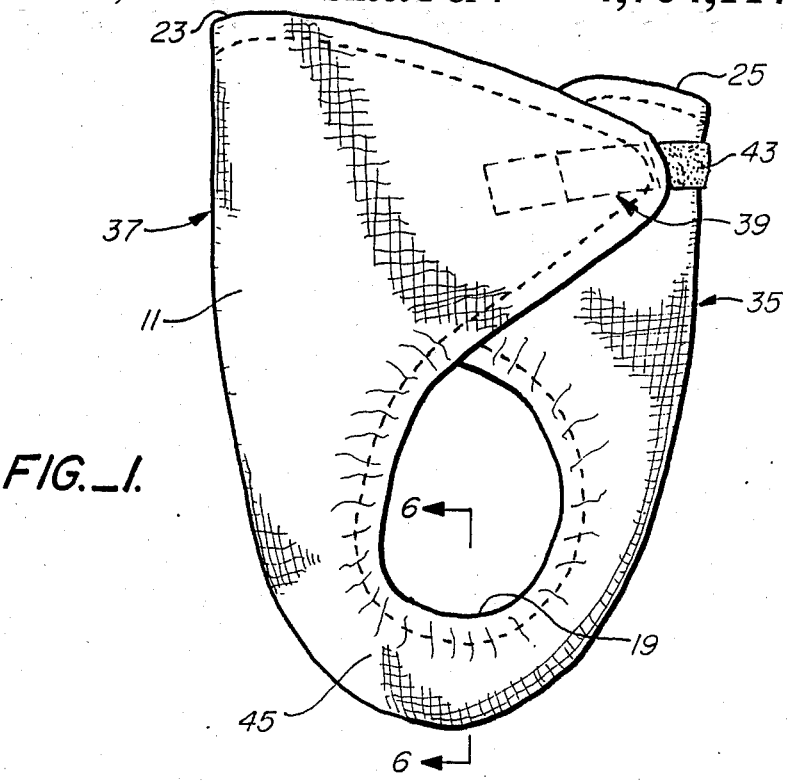
FIG._1.
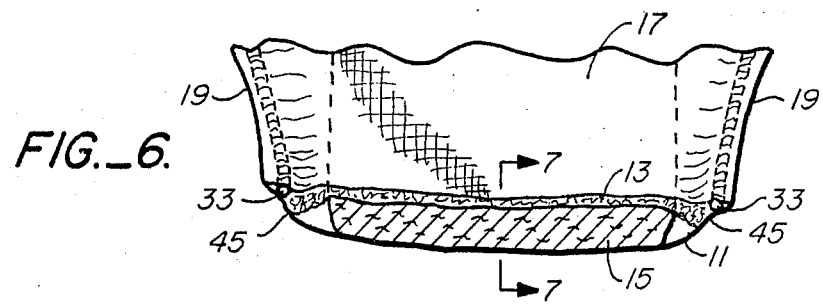
FIG._6.
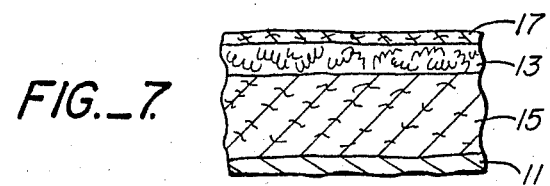
FIG._7.

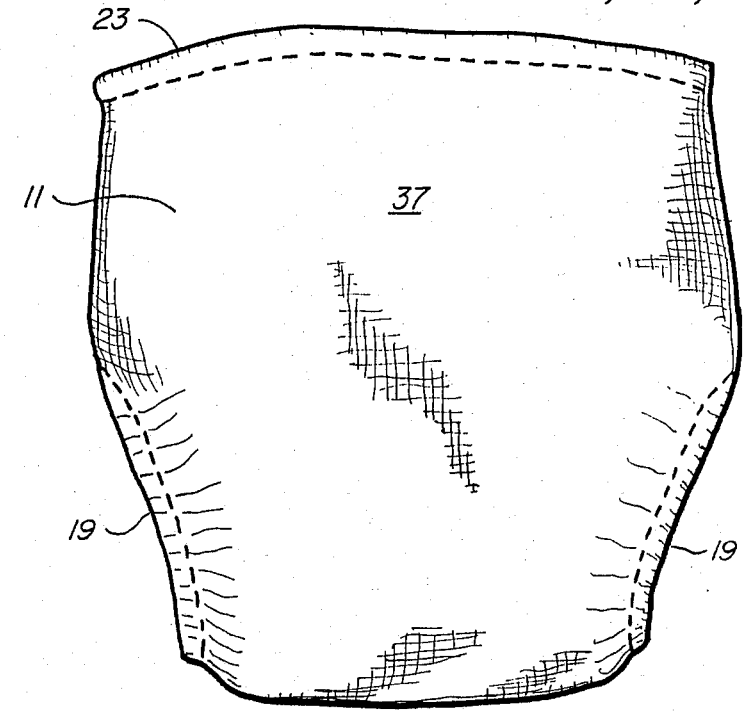
FIG._2.
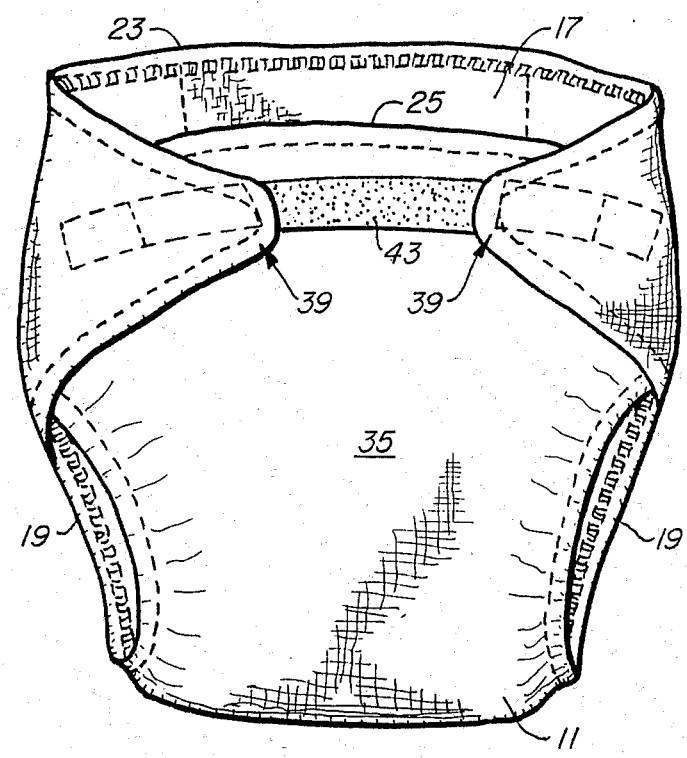
FIG._3.

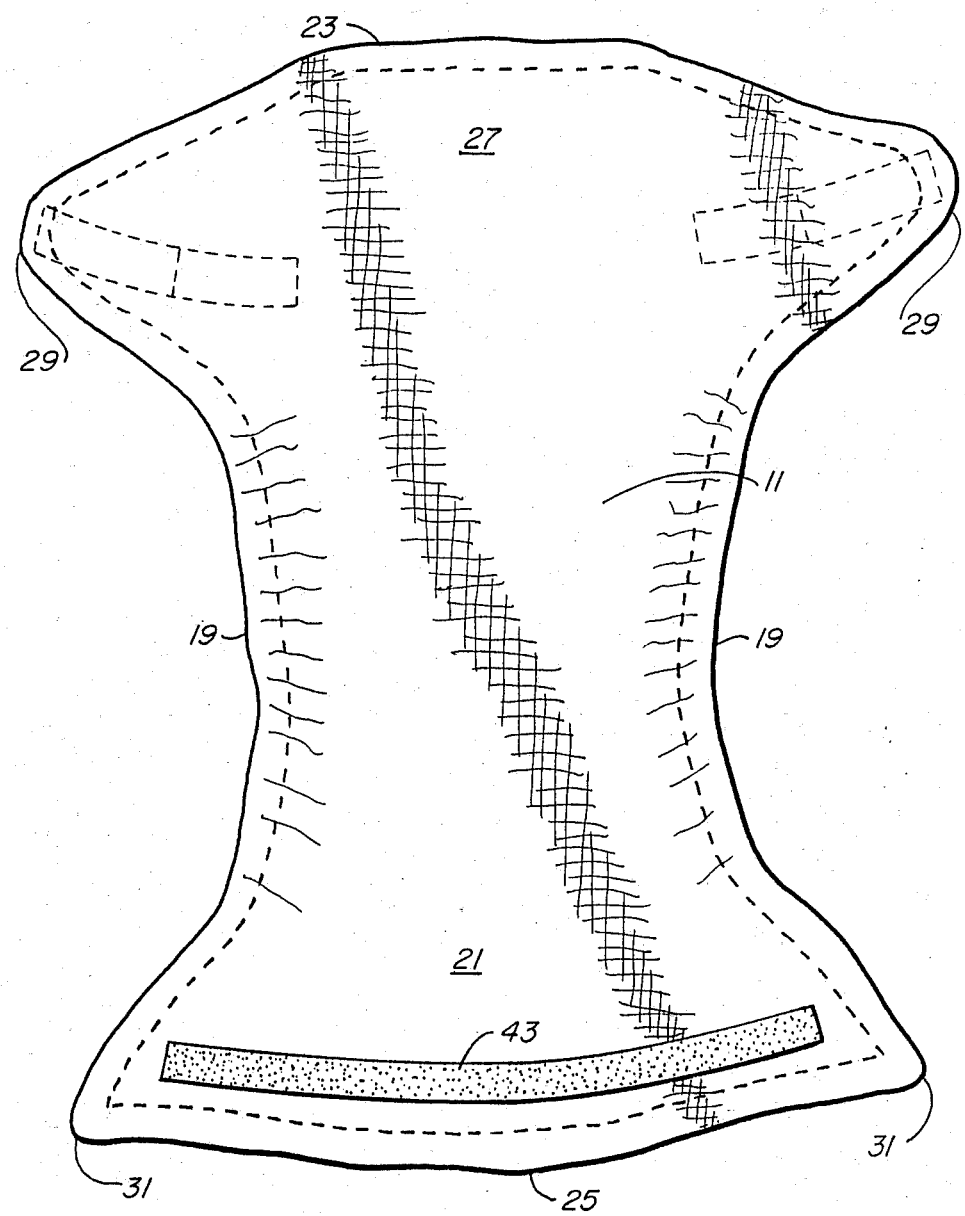
FIG._4.

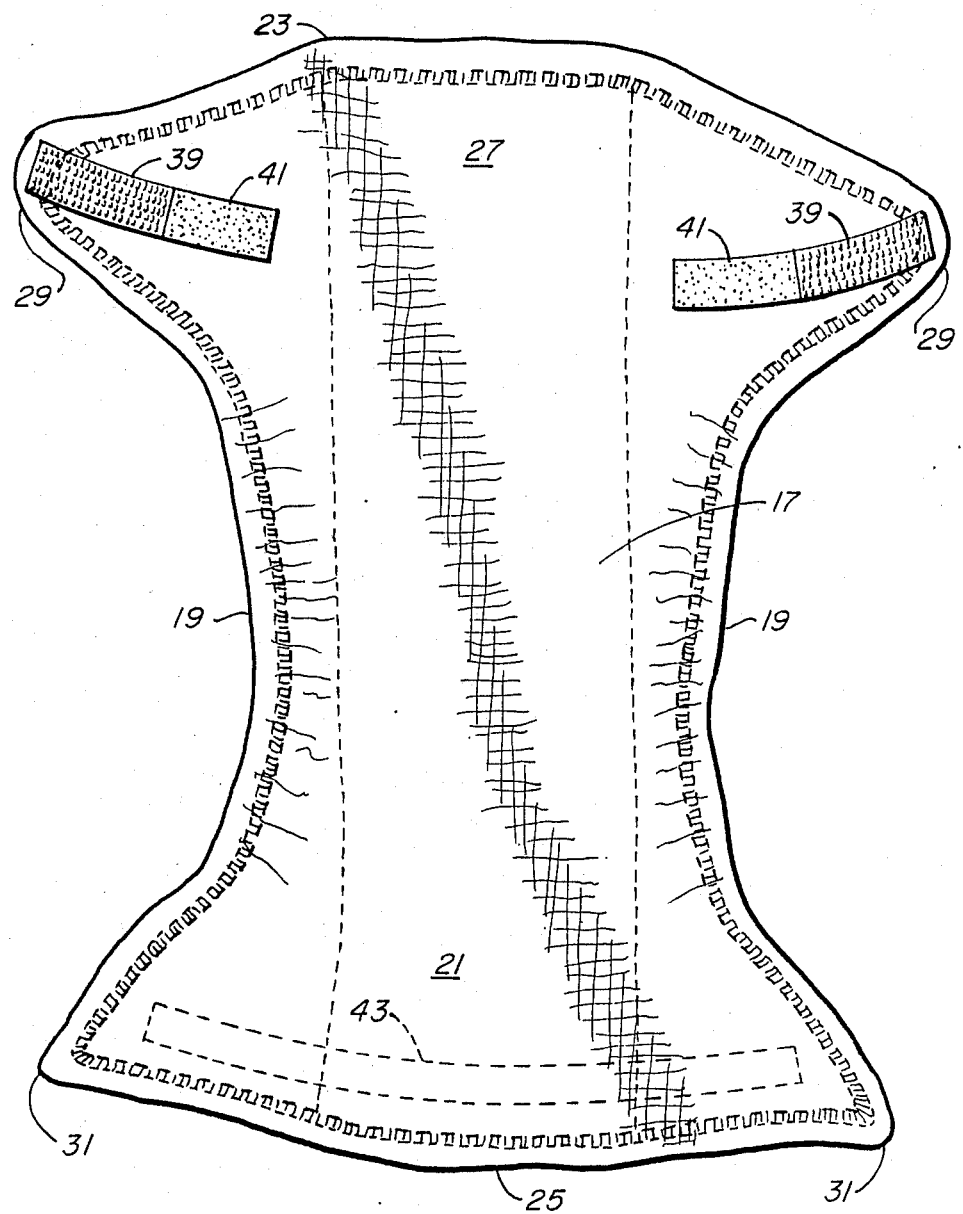
FIG._5.

FORMED AND WASHABLE DIAPER

CROSS-REFERENCES TO RELATED APPLICATIONS

The present invention is related to U.S. patent application Ser. No. 06/365,157 filed Apr. 5, 1982, for a Reusable Fluid Absorption Pad, and is a continuation-in-part of Ser. No. 06/588,349, filed Mar. 12, 1984, now U.S. Pat. No. 4,516,975 issued May 14, 1985 and is a continuation of 660,062 filed Nov. 12, 1984, now abandoned.

BACKGROUND OF THE INVENTION

1. Field of the Invention

The present invention relates to diapers and more particularly to a formed and washable diaper having multiple layers of different types of material for different functions which is reusable and conforms to the body of the wearer.

2. Description of the Prior Art

There are numerous multiple layer fabric diapers on the market such as those described in U.S. Pat. Nos.: 3,646,937; 3,848,594; 3,860,003; and 4,041,951. The problem with these diapers is that all of them are made of disposable materials which cannot be washed and reused because they cannot stand the stress of the washing procedure and the high temperatures of tumble drying which occur in clothes washing and drying machinery. Disposable diapers are very expensive initially but can be washed and reused many times.

A further problem results if a person wants to undo a disposable diaper to check it for deposits: it is almost always necessary to replace the diaper because disengaging the adhesive securement strips usually results in tearing the diaper so it cannot be refastened.

There are other problems with disposable diapers. The chemicals utilized in the fragrances put into the diapers have proven to cause skin irritation and bronchial infection and irritation. Numerous cases of infant deaths have been reported which have been determined to have been due to inhalation of particles and pieces of disposable diapers which were apparently torn or picked off the diaper by the infants when the diapers became wet and lost the tensile strength. Additional deaths been determined to have occurred from suffocation when the diapers became wet and the securement means tore off the diaper ended up covering the infant's face. The present invention has been designed to at least minimize but in most cases eliminate these problems.

SUMMARY OF THE INVENTION

The present invention is a formed and washable diaper comprised of a multiplicity of layers of material including an outer layer forming a moisture barrier cover, a moisture absorbent felt layer forming the frame of the diaper, and a soft inner facing layer made of a non-irritating absorbent washable fabric.

The diaper has a particular body enclosing configuration due to its unique construction which includes an hour-glass outline with each of the hour-glass shaped sides forming a continuous sculpted crescent shaped concave curve. The top and bottom edges are generally curved slightly convex upward and downward respectively. The upper end of the diaper is slightly longer in lateral length than the bottom end whereby when the diaper is placed on the wearer with the top end disposed at the back of the body and with the bottom end pulled up between the wearer's legs and disposed with the bottom end in front on the stomach of the wearer's body, the two edges of the top end of the diaper will wrap around the wearer's body from behind and overlap the two edges at the bottom end of the diaper disposed on the wearer's stomach.

The lateral curved vertically disposed edges of the diaper are provided with a stretched elastic edging which is secured to the material for a portion of the length of the curved edges whereby when the elastic is released, and allowed to retract, the diaper is pulled into a U-shaped configuration.

The outer edges of the inner and felt outer layers of the material are formed generally co-extensive throughout the extent of the configuration of the diaper. The outer layer extends peripherally outward beyond the edges of said co-extensive inner and felt layers to provide a moisture barrier border which extends beyond the edges of the absorbent layers of the diaper.

The tabs formed by the top and bottom lateral edges or corners of the diaper are provided with adjustable strip and grip fasteners for securing the overlapping edges together to hold the diaper on the wearer's body.

OBJECTS OF THE INVENTION

It is therefore an important object of the present invention to provide a formed diaper which conforms to a wearer's body.

It is another object of the present invention to provide a washable diaper which can withstand both the stress of washing in automatic clothes washers and the high temperatures of hot air clothes dryers.

It is a further object of the present invention to provide a reusable diaper which provides a felt absorbent layer for retaining greater amounts of moisture than other reusable diapers.

It is yet another object of the present invention to provide a diaper which is safe, non-irritating, mildew-resistant, and does not require any pins to hold it on the wearer.

It is yet a further object of the present invention to provide a diaper which is adjustable in size and can be easily arranged in a non-snagging configuration for washing.

Other objects of the present invention will become apparent when the description of the preferred embodiment thereof is considered in conjunction with the accompanying drawings.

BRIEF DESCRIPTION OF THE DRAWINGS

FIG. 1 is a side elevation of the formed and washable diaper of the present invention;

FIG. 2 is a rear elevation of the diaper of the present invention;

FIG. 3 is a front elevation of the diaper of the present invention;

FIG. 4 is a bottom plan view of the diaper of the present invention in a stretched out configuration showing the outside thereof;

FIG. 5 is a top plan view of the diaper of the present invention showing the inner side thereof in a stretched out configuration;

FIG. 6 is a partial cross-section of the diaper of the present invention taken along lines 6—6 of FIG. 1; and FIG. 7 is a partial cross-section of the diaper of the present invention taken along lines 7—7 of FIG. 6.

DESCRIPTION OF THE PREFERRED EMBODIMENT

The preferred embodiment of the formed and washable diaper of the present invention has a natural body-enclosing configuration which is due to its unique form of construction. It is substantially form-fitting to a wearer's body. It's primary use is for infants, but with proper sizing it can be used equally well for any incontinent person and geriatric patients. The material utilized in the construction of the diaper of the present invention permits it to be reused through an average of between 30 to 50 and up to 85 washings.

The present invention includes a non-allergenic moisture barrier outer layer 11 which prevents excreted fluids retained by the absorbent layers from passing through the diaper covering to the garments or bedcloths of the wearer. In the preferred embodiment, the outer layer is made of urethane coated 100% nylon taffeta.

The absorbent layer 15 is constructed of felt made from a needle punched rayon and polyester blend. This layer is of uniform thickness but is considerably thicker than the inner and outer layers. It is formed in the shape of a narrow rectangle which in operative position extends fore and aft between the wearer's legs and covers the wearer's crotch area. It functions as a frame for the diaper to hold its shape and maintain its formed configuration once the construction of the diaper has been completed. It supports the other materials which are attached to it.

An intermediate batting layer can be utilized made of a mildew-resistant washable spun rayon and polyester. The material characteristics of the batting permit it to function as a frame for the diaper to hold its shape and maintain its formed configuration once the construction of the diaper has been completed. It supports the other materials which are attached to both sides of it but it is not essential to the diaper construction.

The inner layer 13 17 of the diaper is a soft non-irritating absorbent washable fabric that is disposed next to the skin of the wearer to absorb the excreted fluids and permit them to wick through to the absorbent layer. In the preferred embodiment, it is comprised of 100% cotton, but it has been found that a blend of up to 50% polyester with the cotton will also work satisfactorily.

The diaper has a particular body enclosing configuration due to its construction. This is created by forming the diaper in an outline described as somewhat of an hourglass but with the pinched in sides actually being formed by a continuous sculpted crescent shaped concave curve on each of the lateral edges 19. These edges are narrowed more towards the bottom end 21 of the diaper which end forms the front thereof. The top and bottom edges 23, 25, respectively, of the diaper are also generally curved slightly convex upward and downward respectively. In actual practice, the flat top and bottom edges are tapered slightly toward the center of the diaper to provide the convex configuration.

The upper end 27 of the diaper is slightly longer in lateral length than the bottom end, whereby, when the diaper is placed on the wearer with the top end disposed at the back of the body, and with the bottom end 21 pulled up between the wearer's legs and disposed at the front of the wearer's body on the stomach, the corners of the top end 23 of the diaper will wrap around the wearer's body from behind and overlap the two corners 31 formed by the bottom end of the diaper when it is disposed on the wearer's stomach. This configuration reduces the bulk of material that must be disposed between the wearer's legs.

In addition to providing a configuration which allows uniformity of thickness be disposed on the wearer's body without the bunching up of material, the unique construction of the diaper also causes it to be formed into a body enclosing configuration. This is done by providing the curved lateral vertically disposed edges 19 of the diaper with a stretched elastic edging 33 which is secured to the material of the diaper with an overlock stitch for that portion of the length of the curved edges which is disposed around the wearer's legs. This elastic 33 is stretched during the sewing operation whereby when the elastic is released and allowed to retract to its normal state of rest, the diaper is pulled into a U-shaped configuration. The resulting opposed portions of the U-shaped configuration are the front and rear flaps 35, 37, respectively, of the diaper.

The outer edges of the inner and outer layers, 11, and 17, respectively, of the material forming the diaper are generally co-extensive throughout the extent of the configuration of the diaper. The absorbent layer 15 may not extend fully to the corners of the diaper and yet function fully. The outer layer extends peripherally outward beyond the edges of the co-extensive inner and absorbent felt layers to provide a moisture barrier which extends beyond the edges of the absorbent layers of the diaper. This border prevent prevents the sewn edges of the diaper, which are particularly susceptible to wicking moisture from the absorbent felt layer to the edges of the diaper, from contacting the wearer's skin.

The tabs 29, 31 that are formed by the corners of the diaper, are provided with strip and grip fasteners for securing the overlapping edges together to hold the diaper on the wearer's body. In the preferred embodiment, Velcro brand or similar fasteners are used which when positioned as shown in the drawings provide an adjustable perfect bodyfitting securement means which is on the front of the diaper so that the wearer can be laid on his or her back to fasten the diaper. The wearer's legs are lifted, the top or rear of the diaper is slid underneath, the wearer's legs are allowed to drop on both sides of the diaper, the front flap is pulled up, the two tabs from the rear flap wrap over and press on those that lie on the front, and the diaper is automatically secured to the wearer with no further effort and particularly without pins that could possibly be stuck into the wearer by accident.

A stick strip 43, that interwoven mass of fabric element of the fastener which is engaged by the hooks of the grip element 39, is disposed on the outward side of the front of the diaper proximate the top peripheral edge. This allows a large range of adjustment of the size of the diaper. On the corners of the other end of the diaper, aligned mating pairs of strip and grip tabs are provided with the grip tabs 39 at the outer ends of the corners and the strip tabs 41 adjacent thereto. These pairs of tabs allow the corners of the diaper to be folded over to engage themselves. This keeps the grip portion from snagging any other engageable surface and is particularly helpful during washing of the diapers to keep them from entangling with and snagging each other.

The present invention is 10 to 15 times more expensive per unit than disposable diapers presently on the market, but since it can be reused between 30 to as many as 85 times it is in effect between $\frac{1}{3}$ and 2/17 as expensive as a disposable diaper in overall cost. The benefits of the comfort and safety of having a non-allergenic, pinless diaper, which always retains its tensile strength so it cannot fall or be picked apart when it becomes wet, are self-evident. These advantages are not obtainable from disposable diapers.

Thus, it will be seen from this description of the preferred embodiment of the present invention that the formed and washable diaper disclosed and described herein achieves the objects and advantages attributable thereto, and while the invention has been described in considerable detail, it is not to be limited to such details as set forth except as may be necessitated by the appended claims.

I claim:

1. A formed and washable diaper comprised of
   a multiplicity of layers of material including a urethane coated nylon taffeta outer layer forming a moisture barrier cover,
   an inner facing layer of cotton or cotton blend fabric,
   an intermediate layer of batting made of spun rayon and polyester forming the frame of the diaper, said inner layer and said batting layer formed to be substantially co-extensive throughout the extent of the configuration of said outer layer, said diaper having a particular body enclosing configuration due to its construction which includes an hour-glass outline with each of the hour-glass shaped sides forming a continuous sculpted crescent-shaped concave curve with the top and bottom edges of the diaper being generally curved slightly convex upward and downward respectively, the upper end of said diaper being slightly longer in lateral length than the bottom end whereby when the diaper is placed on the wearer with the top end disposed at the back of the wearer's body and with the bottom end pulled up between the wearer's legs and disposed on the front of the wearer's body on the stomach, the two lateral edges of the top end of the diaper will wrap around the wearer's body from behind and overlap the two lateral edges at the bottom edge of the diaper disposed on the wearer's stomach, the laterally curved vertically disposed edges of the diaper being provided with an elastic edging which is secured to said material for a portion of the length of the curved edges which surround the wearer's leg when the dipaer is disposed in operative position whereby when the elastic is released after being secured to the diaper in a stretched condition along the edge of said diaper and allowed to retract, said diaper is retracted into a U-shaped configuration with the resulting portions being the front and rear flaps of said diaper,
   an intermediate felt layer disposed between the outer layer and the batting layer in the form of a rectangular strip of material which extends for a substantial portion of the length of the diaper between the top and bottom edges and laterally from side to side proximate the sculpted sides of the diaper in the area where the elastic edging is disposed, said felt being made of needle punched rayon and polyester blend, and
   the tabs formed by the top and bottom lateral edges or corners of said diaper being provided with adjustable strip and grip fasteners for securing said overlapping lateral edges together to hold the diaper on the wearer's body.

2. The formed and washable diaper of claim 1 wherein two corners at the same end of the diaper are provided with mating pairs of strip and grip tabs so that the corners of the diaper having the mating pairs of strip and grip tabs can be folded over to engage themselves and keep the grip portion of the tab from snagging any other engageable surface, the other end of said diaper being provided with an elongated strip tab disposed across the front of said diaper to adjustably engage the grip tabs.

3. A washable diaper comprised of a multiplicity of layers of material formed with a narrowed intermediate section which fits between the legs of the wearer, said diaper being narrowed to prevent excessive bunching of material when disposed in operative position, said diaper including
   a coated nylon outer layer forming a moisture barrier cover,
   an intermediate moisture retentive mildew resistant washable felt layer formed in a strip which in operative position extends at least fore and aft between the wearer's legs and covers the wearer's crotch area, and
   an inner facing layer of soft non-irritating absorbent washable fabric, and an intermediate mildew resistant washable layer of batting disposed between said felt layer and said inner facing layer, said inner facing and batting layers being substantially co-extensive throughout the extent of the configuration of said outer layer.

4. The formed and washable diaper of claim 3 wherein the felt layer is a rectangular strip of material made of needle punched rayon and polyester blend and said batting layer is made of spun polyester or a blend spun of materials including polyester.

5. The formed and washable diaper of claim 4 wherein said outer layer is a urethane coated nylon taffeta, said intermediate felt layer extends for a subtantial portion of the length of the diaper and at least from side to side proximate the edges of the diaper in the areas which are disposed to encircle the wearer's legs, and
   said inner facing layer is cotton or a cotton and polyester blend.

6. The formed and washable diaper of claims 1 and 2 wherein said outer layer is formed to extend peripherally outward beyond the edges of said substantially co-extensive inner layers to provide a moisture barrier border which extends slightly beyond the edges of the absorbent layers of said diaper.

7. The formed and washable diaper of claims 1, 2 and 6 wherein said felt layer portion of said diaper is slightly narrower in width in the narrowest portion of said diaper between the top and bottom ends thereof so that the remaining edges of the diaper alongside the felt strip are pulled upward into the middle of the U-shaped diaper when the elastic is released forming parallel vertical side-walls in the bottom of the diaper.

* * * * *